United States Patent
Rusch (10) Patent No.: US 11,338,068 B2
(45) Date of Patent: May 24, 2022

(54) TWO-PART IMPLANTABLE THERAPY DELIVERY DEVICE

(71) Applicant: W. L. Gore & Associates, Inc., Newark, DE (US)

(72) Inventor: Greg Rusch, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 503 days.

(21) Appl. No.: 15/805,789

(22) Filed: Nov. 7, 2017

(65) Prior Publication Data
US 2018/0126042 A1 May 10, 2018

Related U.S. Application Data

(60) Provisional application No. 62/419,100, filed on Nov. 8, 2016.

(51) Int. Cl.
| | |
|---|---|
| *A61L 27/58* | (2006.01) |
| *A61L 27/28* | (2006.01) |
| *A61L 27/54* | (2006.01) |
| *A61L 27/56* | (2006.01) |
| *A61K 9/00* | (2006.01) |
| *A61K 35/12* | (2015.01) |
| *A61L 27/38* | (2006.01) |

(52) U.S. Cl.
CPC .......... *A61L 27/58* (2013.01); *A61K 9/0024* (2013.01); *A61K 35/12* (2013.01); *A61L 27/38* (2013.01); *A61L 27/54* (2013.01); *A61L 27/56* (2013.01); *A61L 2300/412* (2013.01); *A61L 2400/18* (2013.01)

(58) Field of Classification Search
CPC .......... A61L 27/58; A61L 27/38; A61L 27/54; A61L 27/56; A61L 2300/412; A61L 2400/18; A61K 9/0024; A61K 35/12
See application file for complete search history.

(56) References Cited

U.S. PATENT DOCUMENTS

| | | | |
|---|---|---|---|
| 5,626,561 A | 5/1997 | Butler et al. | |
| 5,713,888 A | 2/1998 | Neuenfeldt et al. | |
| 5,787,900 A | 8/1998 | Butler et al. | |
| 5,843,069 A * | 12/1998 | Butler ................... | A61F 2/0004 604/891.1 |

(Continued)

FOREIGN PATENT DOCUMENTS

| | | |
|---|---|---|
| CN | 103025303 A | 4/2013 |
| JP | 1988(S63)-159314 A | 7/1988 |

(Continued)

OTHER PUBLICATIONS

Sandle S., Eizirik D.L., "Culture of Human Pancreatic Islet Cells." in: Jones G.E. (eds) Human Cell Culture Protocols. Methods in Molecular Medicine, vol. 2 (Humana Press, 1996), pp. 391-407. (Year: 1996).*

(Continued)

*Primary Examiner* — Kara D Johnson (57) ABSTRACT

An implantable therapy delivery device that includes a porous pouch and a cell encapsulation device configured to fit inside the porous pouch. The porous pouch may include a bio-absorbable material and/or a vascularization promotor, and the porous pouch may be packaged separately from the cell encapsulation device.

13 Claims, 6 Drawing Sheets

(56) References Cited

U.S. PATENT DOCUMENTS

| | | | |
|---|---|---|---|
| 5,902,745 A * | 5/1999 | Butler | A61F 2/022 |
| | | | 424/424 |
| 5,913,998 A | 6/1999 | Butler et al. | |
| 6,479,066 B1 | 11/2002 | Harpstead | |
| 2008/0128315 A1 | 6/2008 | Buevich et al. | |
| 2014/0014226 A1 | 1/2014 | Green et al. | |
| 2014/0021088 A1 | 1/2014 | Konig et al. | |

FOREIGN PATENT DOCUMENTS

| | | | | |
|---|---|---|---|---|
| JP | 1993(H05)-154195 A | 6/1993 | | |
| JP | 2001-299908 A | 10/2001 | | |
| JP | 2005-169008 A | 6/2005 | | |
| JP | 2009225661 | 10/2009 | | |
| WO | WO199632076 | 10/1996 | | |
| WO | WO-2014036364 A1 * | 3/2014 | | A61L 31/06 |
| WO | WO2014/130953 | 8/2014 | | |

OTHER PUBLICATIONS

Moisture in Packaging. Package Engineering [online], Jun. 1985 [retrieved on Jun. 8, 2020], Retrieved from the Internet:<URL: https://www.sorbentsystems.com/desiccant_info.html>. (Year: 1985).*

De Vos et al., Long-term biocompatibility, chemistry and function of microencapsulated pancreatic islets. Biomaterials, vol. 24, No. 2 (Jan. 2003) pp. 305-312. (Year: 2003).*

International Search Report for PCT/US2017/060492 dated Feb. 9, 2018 and mailed on Feb. 21, 2018.

* cited by examiner

TWO-PART IMPLANTABLE THERAPY DELIVERY DEVICE

FIELD

The present invention relates to the field of medical devices and, in particular, to an implantable device for delivering a biological therapy to a patient.

BACKGROUND

Biological therapies are increasingly viable methods for treating peripheral artery disease, aneurysm, heart disease, Alzheimer's and Parkinson's diseases, autism, blindness, diabetes, and other pathologies.

With respect to biological therapies in general, cells, viruses, viral vectors, bacteria, proteins, antibodies, and other bioactive moieties may be introduced into a patient by surgical or interventional methods that place the bioactive moiety into a tissue bed of a patient. Often the bioactive moieties are first placed in a device that is then inserted into the patient. Alternatively, the device may be inserted into the patient first with the bioactive moiety added later.

Devices for encapsulating biological moieties conventionally include a selectively permeable membrane to contain the therapeutic agent while remaining permeable to nutrients to sustain the agent, waste from the agent, and the therapeutic product produced by the agent. A typical biological response to introduction of these therapeutic devices is the formation of a fibrotic capsule around the device, which can deprive the encapsulated cells of life sustaining exchange of nutrients and waste products with tissues of a patient, and thus limit the performance of the device. The result is usually fatal to encapsulated cells. Furthermore, a fibrotic, capsule encasing a therapeutic device usually makes surgical retrieval of the device difficult.

To avoid formation of this fibrotic capsule, some implantable devices include an external layer that can support vascularization, i.e., vascular tissues of the patient grow into direct, or near direct, contact with the device. This is desirable because the therapeutic product of the device can then be delivered directly to the circulation of the patient through the vascular tissues that are in contact with the device. A considerable drawback to this vascularization is that removal of the device requires surgical dissection of the tissues to expose and remove the device. Surgical dissection of vascular tissues, particularly capillary tissue, can often be a difficult and painful procedure.

Implantation results in some amount of trauma to the patient and period of healing before a therapy provided by the device may be efficacious. Therefore, there remains a need for devices that allow implantation of cells and other biological moieties for providing a biological therapy, where the devices can be quickly integrated into a tissue bed with minimal trauma and without disturbing more of the tissue bed than necessary. There is also a need to avoid impairing the implantation device or harming the biological moieties during or after implantation.

SUMMARY

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

The present invention relates to implantable assemblies for providing a biological therapy to a patient within a tissue bed. The implantable assemblies include a porous pouch for housing a cell encapsulation device. The porous pouch has properties that promote vascularization and/or incorporation of the device into the tissue bed. For example, the porous pouch may include a bio-absorbable material and/or a vascularization promoter. The cell encapsulation device includes a plurality of cells in a cell-sustaining medium. The cell encapsulation device may be stored or processed (grown, matured) in a cell-sustaining medium. Certain elements of the porous pouch, such as the big-absorbable material and the vascularization promotor, are incompatible with the cell-sustaining medium. Advantageously to provide separate environments prior to implantation, the implantable assemblies are maintained as two separate elements, in two separate environments. During implantation the separate, elements may form one implantable assembly.

Described herein are kits including a cell encapsulation device contained within a first, cell-sustaining environment and a porous pouch contained within a second environment, where the second environment is different from the first environment and where the cell encapsulation device is configured to fit inside the porous pouch. The cell-sustaining environment may include a medium conducive to the subsistence of a plurality of cells. In some embodiments, the cell-sustaining medium may be an aqueous medium. In some embodiments, the cell-sustaining medium may include at least one cell nutrient.

In some embodiments, a porous pouch described herein includes a bio-absorbable material. The bio-absorbable material may be, for example, polyglycolide:trimethylene carbonate (PGA:TMC), polyalphahydroxy acid such as polylactic acid, polyglycolic acid poly (glycolide), and poly (lactide-co-caprolactone), poly(caprolactone) poly(carbonates), poly(dioxanone), poly(hydroxybutyrates), poly(hydroxyvalerates), poly(hydroxylbutyrates-co-valerates), and copolymers and blends thereof. In some embodiments, a cell-sustaining environment is detrimental to the big-absorbable material. In some embodiments, the bio-absorbable material is configured to degrade upon contact with moisture. Also, the big-absorbable material may be temperature dependent, such as, for example, more pliable in a warmer environment (e.g., body temperature) and less pliable in a cooler environment (e.g., room temperature). Accordingly, in some embodiments, the second environment is a dry environment and/or a temperature controlled environment. The dry environment may include a desiccant for maintaining a reduced level of moisture in the environment.

In some embodiments, the porous pouch includes a polymer selected from alginate, cellulose acetate, polyalkylene glycols such as polyethylene glycol and polypropylene glycol, panvinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene, modified polytetrafluoroethlyene polymers, tetrafluoroethylene (TFE) copolymers, porous polyalkylenes such as porous polypropylene and porous polyethylene, porous polyvinylidene fluoride, porous polyester sulfone, porous polyurethanes, porous polyesters, and copolymers and combinations thereof. In exemplary embodiments, the polymer is porous polytetrafluoroethylene, porous polypropylene, porous polyethylene, porous polyvinylidene fluoride, and combinations thereof. In some embodiments, the porous material may be included in addition to the bio-absorbable material.

In some embodiments, the porous pouch includes a plurality of pores of a size sufficient to permit growth of vascular tissue from a patient within the plurality of pores. In addition, the porous pouch may include a second layer that includes a plurality of pores having a size sufficient to restrict or prohibit the growth of vascular tissue from the patient. The inclusion of a non-vascularizing layer may assist preserving space within the porous pouch such that the cell encapsulation device can be removed and reinserted one or more times. The porous pouch may also comprise a vascularization promoter. The vascularization promoter may be water soluble.

In some embodiments, the porous pouch is configured to retain the cell encapsulation device inside the porous pouch. The porous pouch and/or the cell encapsulation device may be configured to allow insertion of the cell encapsulation device into the pouch and to allow subsequent removal of the cell encapsulation device from the pouch. In some embodiments, the porous pouch is configured to be attachable to the cell encapsulation device.

Also described herein are implantable devices that includes a porous pouch including a bio-absorbable material and a cell encapsulation device inside the porous pouch. The cell encapsulation device is configured to fit inside the porous pouch. In some embodiments, the bio-absorbable material may have the capability to generate reactive oxygen species (ROS) at different levels in the body.

In some embodiments, the porous pouch includes a bio-absorbable material that may be polyglycolide:trimethylene carbonate (PGA:TMC), polyalphahydroxy acid such as polylactic acid, polyglycolic acid poly (glycolide), and poly (lactide-co-caprolactone), poly(caprolactone), poly(carbonates), poly(dioxanone), poly (hydroxybutyrates), poly(hydroxyvalerates), poly(hydroxybutyrates-co-valerates), and copolymers and, blends thereof. The bio-absorbable material may be configured to degrade upon contact with moisture.

In some embodiments, in addition to the bio-absorbable material, the porous pouch may further include a polymer selected from polyethylene glycol and polypropylene glycol, panvinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene (PTFE), modified polytetrafluoroethylene polymers, tetrafluoroethylene (TFE) copolymers, porous polyalkylenes such as porous polypropylene and porous polyethylene, porous polyvinylidene fluoride, porous polyester sulfone, porous polyurethanes, porous polyesters, and copolymers and combinations thereof.

In some embodiments, the porous pouch includes a plurality of pores of a size sufficient to permit growth of vascular tissue from a patient within the plurality of pores. The porous pouch may also include a vascularization promoter. The vascularization promoter may be water soluble.

In some embodiments, the porous pouch and/or the cell encapsulation device are configured to allow insertion of the cell encapsulation device into the porous pouch and subsequent removal of the cell encapsulation device from the porous pouch. The porous pouch may be configured to be attached to the cell encapsulation device. In some embodiments, the porous pouch can be opened to insert or access a cell encapsulation device.

DETAILED DESCRIPTION

Described herein are implantable assemblies for delivering a biological therapy to a patient. The assemblies include a porous pouch and a cell encapsulation device configured to fit inside the porous pouch, such that the combination of the porous pouch and cell encapsulation device may be implanted into a patient (simultaneously or sequentially), such as into a tissue bed, to provide biological therapy to the patient. The porous pouch may include a bio-absorbable material and/or a vascularization promotor, and the porous pouch may be packaged separately from the cell encapsulation device.

The cell encapsulation device is designed to include a living biological moiety that will provide a biological therapy to a patient once implanted. Biological moieties, suitable for encapsulation and implantation using the devices described herein include cells, viruses, viral vectors, bacteria, proteins, antibodies, and other bioactive moieties. For simplicity, herein the biological moiety is referred to as a cell, but nothing in this description limits the biological moiety to cells or to any particular type of cell, and the following description applies, also to biological moieties that are not cells. As used herein the term "cell encapsulation device" refers to an implantable device that may include cells or any other biological moiety that might provide a biological therapy to a patient.

Various types of prokaryotic and eukaryotic cells may be used with the cell encapsulation devices described herein. In some embodiments, the cells secrete a therapeutically useful substance, Such substances include hormones, growth factors, trophic factors, neurotransmitters, lymphokines, antibodies, or other cell products which provide a therapeutic benefit to the device recipient. Examples of such therapeutic cell products include, but are not limited to, insulin, growth factors, interleukins, parathyroid hormone, erythropoietin, transferrin, and Factor VIII. Non-limiting examples of suitable growth factors include vascular endothelial growth factor, platelet-derived growth factor, platelet-activating factor, transforming growth factors, bone morphogerietic protein, activin, inhibin, fibroblast growth factors, granulocyte-colony stimulating factor, granulocyte-macrophage colony stimulating factor, glial cell line-derived neurotrophic factor, growth differentiation factor-9, epidermal growth factor, and combinations thereof.

Once cells are introduced to the cell encapsulation device the cell encapsulation device remains in a cell-sustaining environment until implantation so that the cells will survive and remain able to produce the therapeutic agent to be delivered to the patient. A cell-sustaining environment as used herein is meant to denote any environment that maintains cells in a condition such that once implanted, they can provide the desired therapeutic agent to the patient. It is to be noted that in some embodiments, the cells may be microencapsulated (i.e., individually coated).

The implantable assembly also includes a porous pouch for accepting and retaining the cell encapsulation device within a tissue bed. The porous pouch has a luminal region for receiving a cell-encapsulation device. The porous pouch has properties that promote vascularization and/or incorporation of the pouch into the tissue bed. For example, the porous pouch may include a bio-absorbable material and/or a vascularization promoter. Elements such as bio-absorbable materials and vascularization promoters, however, may be incompatible with a cell-sustaining environment. For example, the bio-absorbable material may begin to degrade in the presence of water. In that case, if the cell-sustaining environment includes water, exposing the porous pouch to the cell-sustaining environment could cause the bio absorbable material in the porous pouch to degrade prematurely (e.g., before insertion into a patient). If the porous pouch is incompatible with the cell-sustaining medium required for the cell encapsulation device, the porous pouch and the cell-sustaining medium must be separate until implantation or until within an acceptable time prior to implantation.

Described herein are kits including a cell encapsulation device contained within a first, cell-sustaining environment and a porous pouch contained within a second environment, where the second environment is different from the first environment and where the cell encapsulation device is configured to fit inside the porous pouch.

The cell-sustaining environment may include a medium conducive to the subsistence of a plurality of cells. The optimum environment may differ depending on the identity of the cells, the length of time the device may be in storage prior to implantation, a desire to advance or retard cell maturation, susceptibility of a component in the porous pouch to the cell sustaining or ambient environment, and other factors known to a person skilled in the art. The cell-sustaining medium may maintain the cells for a period of time prior to and/or after implantation such that the cells remain, capable of providing a therapeutic agent to a patient, after implantation. The cell-sustaining medium may also promote the growth of the cells. In some embodiments, the cell-sustaining medium may be an aqueous medium. In some embodiments, the cell-sustaining medium may include at least one cell nutrient. For example, the cell-sustaining medium may include one or more amino acids, vitamins, sugars, and/or inorganic ions (e.g., sodium, potassium, calcium, copper, and/or zinc). In some embodiments, the medium must be maintained at, above, or below a certain temperature.

The kits described herein also include a porous pouch configured to receive and retain the cell, encapsulation device within a tissue bed of a patient. In the kit, the porous pouch is contained within a second environment that is different from the first, cell-sustaining environment. In some embodiments, a porous pouch described herein includes a bio-absorbable material. The bio-absorbable material degrades and resorbs into the body after the porous pouch is placed in the body. There should be little or no degradation prior to implantation. In some embodiments only a portion of the porous pouch is formed from the bio-absorbable material, such that when the bio-absorbable material resorbs, the pouch retains some structure for housing a cell encapsulating device. In other embodiments, the bio-absorbable material makes up all, or substantially all, of the porous pouch such that no pouch structure remains after the bio-absorbable material resorbs.

The bio-absorbable material may fully resorb quickly (e.g., in only a few days or months) or may require significantly longer (e.g. years) to fully resorb. The resorption rate of the bio-absorbable material will depend on the identity of the material and the biological environment and can be selected by a person skilled in the art as needed. The bio-absorbable material may be, for example, polyglycolide: trimethylene carbonate (PGA:TMC), polyalphahydroxy acid, polylactic acid, polyglycolic acid, or copolymers or blends thereof. The bio-absorbable material may be formed as a solid (molded, extruded, or crystals), a coating (e.g. on the porous pouch), a self-cohered web, a raised webbing, or a screen. Advantageously, certain bio-absorbable materials provide a slow bio-absorption profile that can be used to instruct vascularization and other tissue ingrowth into various components of the implantable porous pouch to anchor the porous pouch in the implantation site. For example, the bio-absorption profile may be slower than the rate of vascularization. In addition, a slow degradation profile may allow for ease of explant/removal of the pouch.

In some embodiments, the bio-absorbable material may have the capability to generate reactive oxygen species (ROS) at different levels in the body. ROS have been shown to promote various cell responses in the body, including, but not limited to, inhibiting or promoting cell proliferation, differentiation, migration, apoptosis, and angiogenesis. ROS generating materials can be made according to the teachings set forth in, for example, U.S. Pat. No. 9,259,435 to Brown, et al.

In some embodiments, a cell-sustaining environment is detrimental to the bio-absorbable material. Thus, the second environment differs from the first, cell-sustaining environment. In some embodiments, the bio-absorbable material is configured to degrade upon contact with moisture. The dry environment need only be dry enough to prevent detrimental degradation of the bio-absorbable material prior to implantation. In some embodiments, the dry environment has a reduced level of moisture as compared to ambient conditions. The dry environment may include a desiccant for maintaining a reduced level of moisture in the dry environment. Also, the bio-absorbable material may be temperature dependent, such as, for example, the bio-absorbable material may be more pliable in a warmer environment (e.g. body temperature) and less pliable in a cooler environment (e.g., room temperature). Accordingly, in some embodiments, the second environment may be a dry and/or temperature controlled environment.

In some embodiments, the porous pouch includes a polymeric material. The polymer material may be selected from alginate, cellulose acetate, polyalkylene glycols such as polyethylene glycol and polypropylene glycol, panvinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene, modified polytetrafluoroethlyene polymers, tetrafluoroethylene (TFE) copolymers, porous polyalkylenes such as porous polypropylene and porous polyethylene, porous polyvinylidene fluoride, porous polyester sulfone, porous polyurethanes, porous polyesters, porous polyvinylidene fluoride and copolymers and combinations thereof. The polymer material may be selected from porous polytetrafluoroethylene (PTFE) or expanded PTFE (ePTFE), porous polypropylene, porous polyethylene, porous polyvinylidene fluoride, and combinations thereof. In some embodiments, the polymer may be expanded PTFE (ePTFE), expanded polypropylene, expanded polyethylene, or a combination thereof.

Useful ePTFE materials may have a microstructure including nodes, fibrils, and voids between the nodes and fibrils. PTFE, polypropylene, polyethylene, and/or polyvinylidene fluoride may be included in addition to the bio-absorbable material. For example, the bio-absorbable material may be copolymerized or blended with the polymer. In some embodiments, the bio-absorbable material may be present in voids of an ePTFE or other polymeric material, for example as a powder. In some embodiments, the bio-absorbable material may be a coating on the polymer.

In some embodiments, the porous pouch includes a plurality of pores of a size sufficient to permit growth of vascular tissue from a patient within the plurality of pores. In some non-limiting examples, the pore size of the porous pouch is greater than about 5.0 microns as measured by porometry. Ingrowth of vascular tissues through the porous pouch facilitates nutrient transfer from the body to the cells encapsulated in the cell encapsulation device, and the material of the porous pouch is sometimes referred to herein as a vascularizing material. In one embodiment, the porous pouch may contain two, layers, namely, one layer that has a pore size sufficient to permit the ingrowth of vascular tissues (e.g., a vascularizing layer) and one layer that has a pore size sufficient to restrict ingrowth vascular tissue (e.g., a non-vascularizing layer). The presence of a non-vascularization layer may help to preserve the space within the porous pouch such that the cell encapsulation device can be removed and re-inserted one or more times.

The porous pouch may also comprise a vascularization promoter to promote angiogenesis, or the formation of blood vessels, within the porous pouch. Useful vascularization promoters are known to persons skilled in the art and include, but are not limited to, vascular endothelial growth factor (VEG-F), fibroblast growth factor (FGF), matrix metalloproteinase (MMP), angiopoletins (e.g. Ang1 and Ang2), delta-like ligand 4 (Dll4), and class 3 semaphorins (SEMA3s).

The vascularization promoter may be water soluble. In embodiments where the vascularization promoter is water soluble, storing the porous pouch in an aqueous cell-sustaining environment would cause the vascularization promoter to leach out of the porous pouch and would reduce the amount and effectiveness of the vascularization promotor once the porous pouch is implanted. Accordingly, in some embodiments, porous pouches that include vascularization promotors are stored in an environment different from the cell-sustaining environment in which the cell encapsulation device is stored. In some embodiments, a porous pouch including a vascularization promotor is stored in a dry environment. The dry environment need only be dry enough to prevent detrimental leaching of the vascularization promoter from the porous pouch prior to implantation. In some embodiments, the dry environment has a reduced level of moisture as compared to ambient conditions. The dry environment may include a desiccant for maintaining a reduced level of moisture in the dry environment.

The shape of the porous pouch is not limited, but in some embodiments will conform to the shape of a cell encapsulating device to be inserted into and contained by the pouch. At different times, however, one porous pouch may contain different cell encapsulation devices, and at times may include one or more dummy devices. For example, when the porous pouch is initially implanted, it may include a dummy device to simulate the presence of a cell encapsulation device but without living cells. Once vascularization has occurred and nutrients from the body are available, the dummy device may be replaced with a cell encapsulating device including cells. Such a dummy device might be useful where cells would not be expected to survive an initial period of implantation prior to vascularization of the porous pouch. Additionally, in some embodiments, different cell encapsulation devices may be inserted into a single porous pouch to provide different therapies simultaneously or sequentially. Thus, the porous pouch should be of a shape to accept and retain any cell encapsulation device a clinician expects to use.

In some embodiments, the porous pouch may include an edge or tip along a portion of the porous pouch for facilitating implantation. The edge or tip may be a material that is solid (i.e. non-porous) and/or more dense that the material making up the remainder of the pouch. The edge or tip may be tapered to assist implantation of the pouch into a tissue bed. In some embodiments, the edge or tip is fully resorbable.

In some embodiments, the porous pouch is configured to retain the cell encapsulation device inside the porous pouch. In some embodiments, the porous pouch is configured to be attachable to the cell encapsulation device. The porous pouch and/or the cell encapsulation device may be configured to allow insertion of the cell encapsulation device into the pouch and to allow subsequent removal of the cell encapsulation device from the pouch. Thus, in some embodiments, the porous pouch includes one or more openings through which a cell encapsulation device may be placed, retrieved, and replaced in the porous pouch. The openings may be resealable.

In some embodiments, a resealable port is secured to an opening in the porous pouch. A resealable port may have any shape suitable for facilitating placement, retrieval, and replacement of a cell encapsulation device in the porous pouch. In some embodiments, commercially available fittings, such as Luer-lok connectors, are useful as an resealable ports in the containment apparatus described herein. In some embodiments, the resealable port is a hollow cylindrically shaped fitting having a first portion that fits snugly inside an end of the porous pouch and a second portion that extends outside the porous pouch. In some embodiments, the resealable port is an opening in a porous pouch with one or more flexible pieces, or flaps, of porous polymeric material positioned to cover and close the opening. The flaps may be formed as part of the apparatus or may be attached to the apparatus subsequent to its initial construction.

In some embodiments, a resealable opening may be repeatedly opened and closed with a seal. Useful seals include, but are not limited to, caps, plugs, clamps, compression rings, and valves. In some embodiments, a cap may be used to close an opening in a porous pouch. The seal may be attached to the resealable opening with friction, by clamping, or with any other sealing device known to a person skilled in the art. Depending on the intended use of the apparatus, the resealable opening may be sealed to create a hermetical seal, a fluid-tight seal, or a non-fluid-tight seal. In some embodiments, a cell encapsulation device intended for permanent or long term implantation in a patient, may be sealed with a hermetical or a fluid-tight seal.

Cell encapsulation devices suitable for use in the embodiments described herein are not limited, but include any device useful for housing a plurality of cells, or other biological moieties that may provide a therapeutic agent to a patient when implanted in the patient. In some embodiments, a cell encapsulation device suitable for use in the disclosed assemblies includes any device useful for maintaining cells, or other biological moieties, in a discrete space while permitting passage of cell nutrients and waste products in and out of the device.

Figure 1:
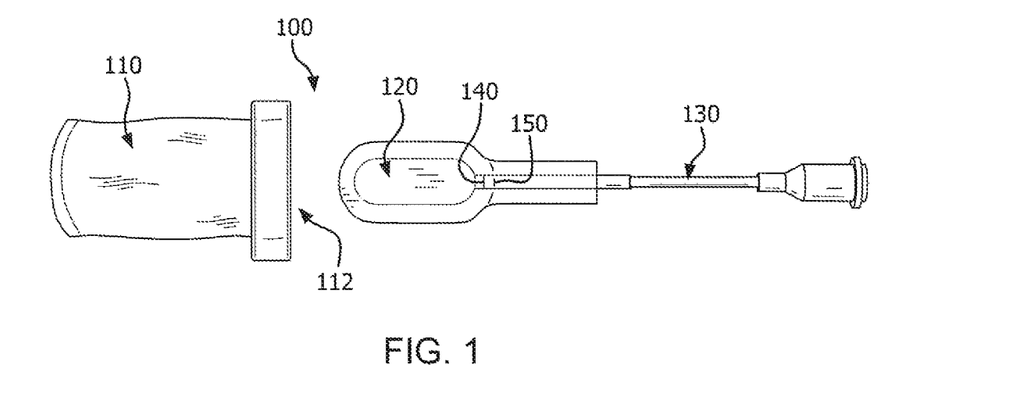
FIG. 1 is a top view of an implantable assembly including a porous pouch and a cell encapsulation device according to embodiments described herein.

FIG. 1 shows one embodiment of an implantable assembly 100 as described herein, including a porous pouch 110 and a cell encapsulation device 120. The cell encapsulation device 120 is shown with a filling needle 130 for injecting cells (not shown) into the encapsulation device 120. Prior to insertion into the porous pouch 110, the encapsulation device 120 is sealed at a sealing region 140 and the needle 130 is removed. Additionally, the encapsulation device may be trimmed at a trimming area 150 that is external to the sealing region to remove extraneous material. The porous pouch 110 includes one open end 112 that is molded for engaging, with a cap (not shown). In some embodiments, a molding for engaging with a cap may be a thermoplastic or thermoset that is attached to or over molded onto the porous pouch. In other embodiments, the porous pouch may be formed into a solid structure for engaging with the cap.

Figure 2:
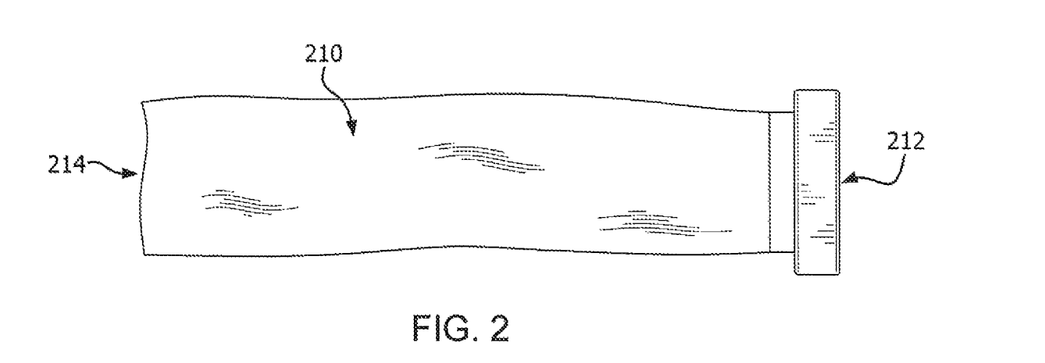
FIG. 2 is a top view of a porous pouch according to embodiments described herein.

FIG. 2 shows an embodiment of a porous pouch 210 as described herein. The pouch has an open, molded end 212 for engaging with a cap (not shown) and a sealed end 214.

Figure 3:
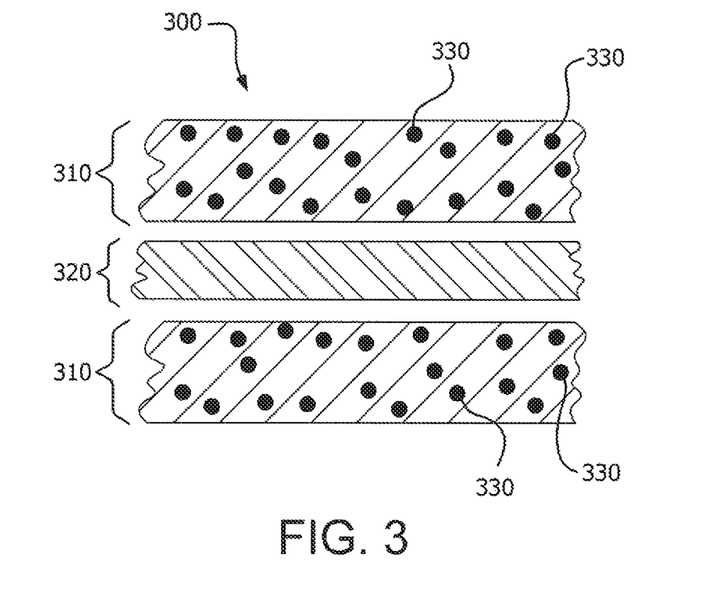
FIG. 3 is a partial cross-sectional view of one embodiment of an assembly including a vascularization promotor distributed within the porous pouch according to embodiments described herein.

FIG. 3 is a partial cross-sectional view of one embodiment of an assembly 300 as described herein. A porous pouch 310 surrounds a cell encapsulation device 320. The porous pouch 310 includes a vascularization promotor 330 distributed within the material forming the porous pouch 310.

Figure 4:
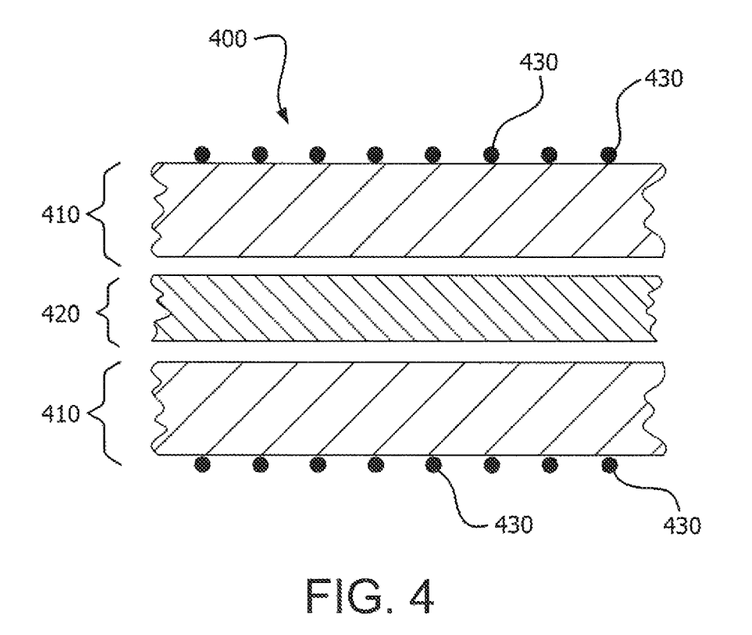
FIG. 4 is a partial cross-sectional view of one embodiment of an assembly including a vascularization promotor on an external surface of the porous pouch according to embodiments described herein.

FIG. 4 is a partial cross-sectional view of one embodiment of an assembly 400 as described herein. A porous pouch 410 surrounds a cell encapsulation device 420. The porous pouch 410 includes a vascularization promotor 430 distributed on the external surface of the porous pouch 410.

Figure 5:
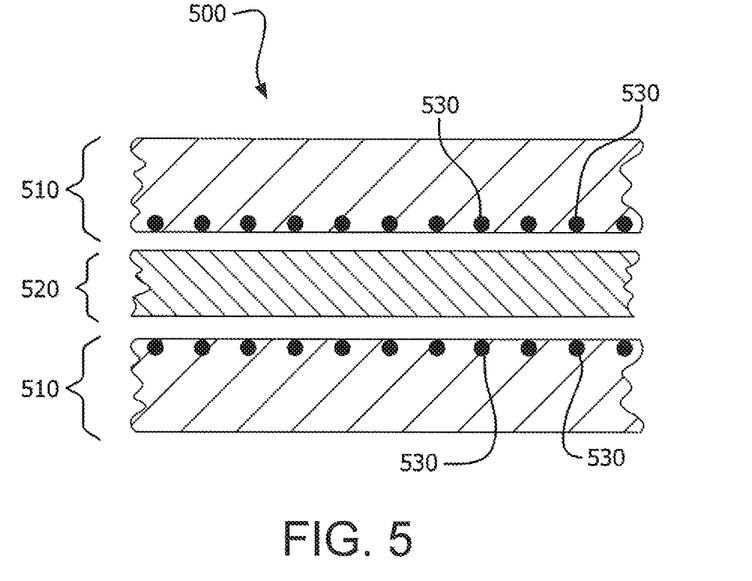
FIG. 5 is a partial cross-sectional view of one embodiment of an assembly including a vascularization promotor on, an internal surface of the porous pouch according to embodiments described herein.

FIG. 5 is a partial cross-sectional view of one embodiment of an assembly 500 as described herein. A porous pouch 510 surrounds a cell encapsulation device 520. The porous pouch 510 includes a vascularization promotor 530 distributed on the internal surface of the porous pouch 510.

Figure 6:
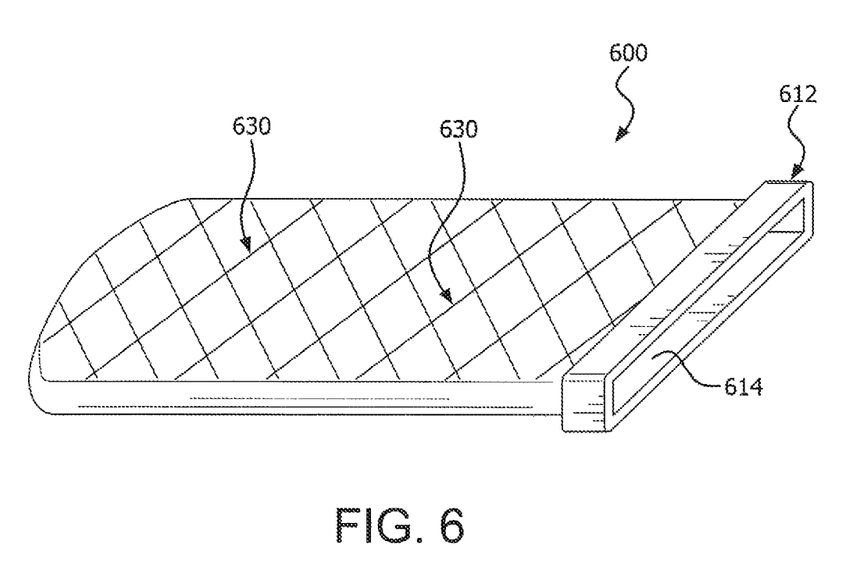
FIG. 6 is a perspective view of one embodiment of a porous pouch including a grid of bio-absorbable material according to embodiments described herein.

FIG. 6 is a perspective view of one embodiment of a porous pouch 610 as described herein. The porous pouch 610 has a molded end 612 for engaging with a cap (not shown). The porous pouch 610 includes an opening 614 for accepting a cell encapsulation device (not shown). The porous pouch also has a grid of bio-absorbable material 630.

Figure 7:
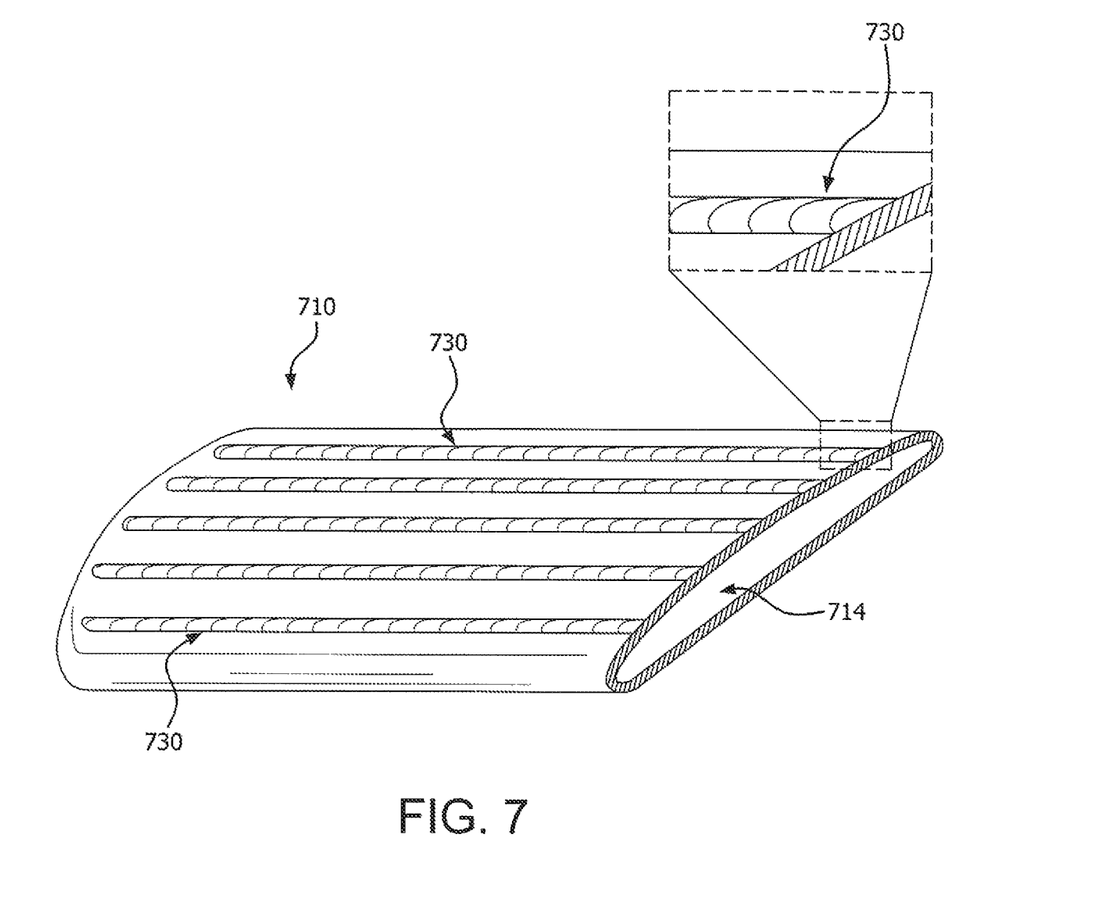
FIG. 7 is a perspective view of one embodiment of a porous pouch including bio-absorbable ridges according to embodiments described herein.

FIG. 7 is a perspective view of one embodiment of a porous pouch 710 as described herein. The porous pouch 710 has an open end 714 for accepting a cell encapsulation device (not shown). The porous pouch also has bio-absorbable ridges 730 to add stiffness during implantation.

Figure 8:
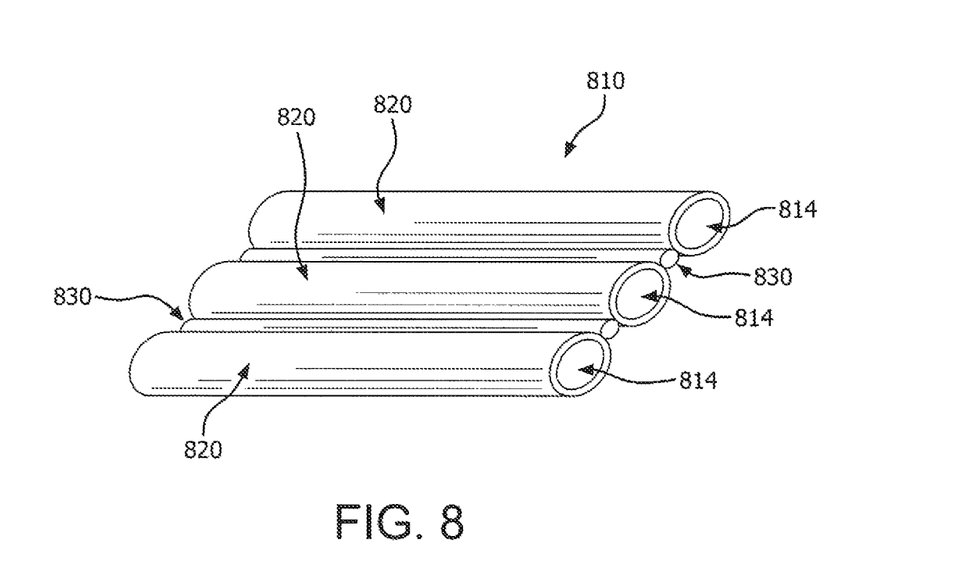
FIG. 8 is a perspective view of one embodiment of a porous pouch in the shape of three adjacent and connected tubes for receiving cylindrical cell encapsulation devices and also including a bioabsorbable material according to embodiments described herein.

FIG. 8 is a perspective view of one embodiment of a porous pouch 810 as described herein. The porous pouch 810 has openings 814 for accepting one or more cell encapsulation devices (not shown). In the embodiment shown in FIG. 8, the porous pouch 810 is in the shape of three adjacent and connected tubes 820 for receiving cylindrical cell encapsulation devices (not shown). Between the tubes 820 is a bio-absorbable material 830. The bio-absorbable material 830 connects the tubes 820 and can provide stiffness to the porous pouch 810 during implantation.

Figure 9:
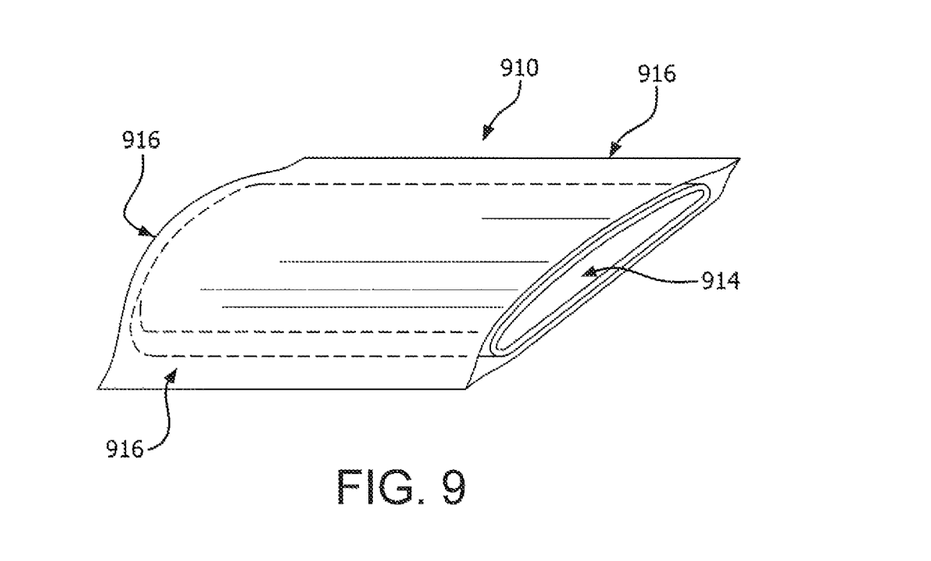
FIG. 9 is a perspective view of one embodiment of a porous pouch having a sharpened edge to aid implantation according to embodiments described herein.

FIG. 9 is a perspective view of one embodiment of a porous pouch 910 as described herein. The porous pouch 910 has a sharpened edge 916 to aid implantation. The sharpened edge 916 may be formed from a bio-absorbable material. The porous pouch 910 has an opening 914 for accepting a cell encapsulation device (not shown).

Figure 10:
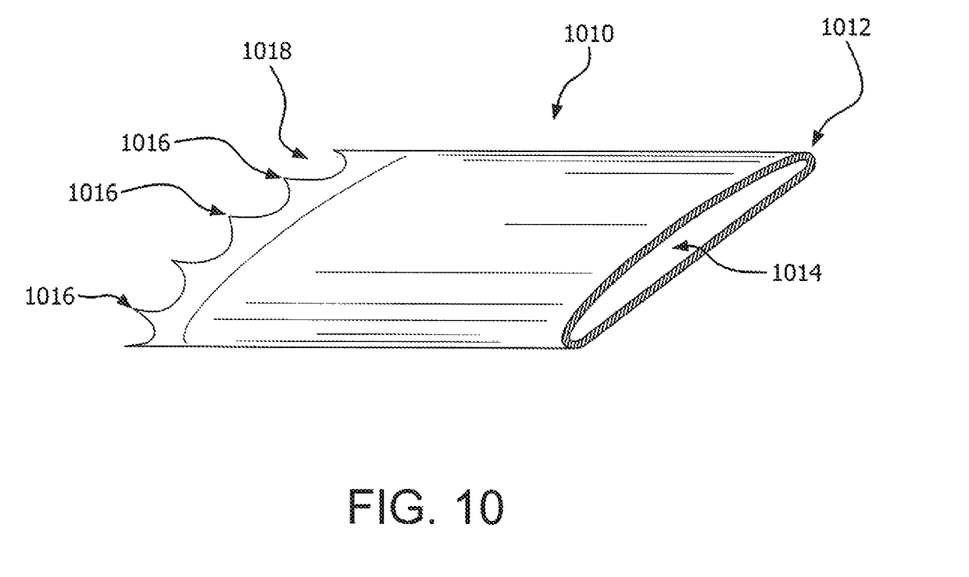
FIG. 10 is a perspective view of one embodiment of a porous pouch having sharpened tips on one end to aid implantation according to embodiments described herein.

FIG. 10 is a perspective view of one embodiment of a porous pouch 1010 as described herein. The porous pouch 1010 has sharpened tips 1016 on one end 1018 to aid implantation. The sharpened tips 1016 may be formed from a bio-absorbable material. The porous pouch 1010 has an opening 1014 at the other end 1012 for accepting a cell encapsulation device (not shown).

The porous pouch and cell delivery device may be inserted into a tissue bed together or separately. Non-limiting examples of tissue beds where the assembly may be implanted include subcutaneous, adipose, long bone, and central nervous system. As non-limiting examples, the tissue may be liver, skin, brain, thymus, pancreas, spleen, testes, kidney, portal vein, muscle, or heart. In some embodiments, the porous pouch may be inserted into the tissue bed first, and subsequently the cell encapsulation device may be inserted into the porous pouch. In some embodiments, the cell encapsulation device may subsequently be removed from the pouch and a different cell encapsulation device inserted to provide continued therapy using the same or different set of cells. In some embodiments, a dummy device (not including living cells) may be inserted into the porous pouch.

The invention may also be described by the following:

1. A kit comprising a cell encapsulation device contained within a first environment, wherein the first environment is a cell-sustaining environment; and a porous pouch contained within a second environment, wherein the second environment is different from the first environment, wherein the cell encapsulation device is configured to fit inside the porous pouch.

2. The kit of claim 1, wherein the cell-sustaining environment comprises a medium conducive to the subsistence of a plurality of cells.

3. The kit of claim 1 or 2, wherein the medium is an aqueous medium.

4. The kit of any one of claim 1, 2, or 3, wherein the medium comprises at least one cell nutrient.

5. The kit of any previous claim, further comprising a plurality of cells in said cell-sustaining environment.

6. The kit of any previous claim, wherein said cells are microencapsulated.

7. The kit of any previous claim, wherein the second environment is at least one member selected from a dry environment and a temperature controlled environment.

8. The kit of any previous claim, wherein the dry environment comprises a desiccant.

9. The kit of any previous claim, wherein the porous pouch comprises a bio-absorbable material.

10. The kit of any previous claim, wherein the bio-absorbable material is configured to degrade upon contact with moisture.

11. The kit of any previous claim, wherein said pouch has a sharpened edge or sharpened tips to aid in implantation into a tissue bed.

12, The kit of any previous claim, wherein the porous pouch comprises a plurality of pores of a size sufficient to permit growth of vascular tissue from a patient, within the plurality of pores.

13. The kit of any previous claim, wherein the porous pouch further comprises a non-vascularizing layer comprising a plurality of pores having a pore size that restricts ingrowth of vascular tissues into the plurality of pores.

14. The kit of any previous claim, wherein the porous pouch comprises a vascularization promoter.

15. The kit of any previous claim, wherein the porous pouch retains the cell encapsulation device inside the porous pouch.

16. The kit of any previous claim, wherein the bio-absorbable material generates reactive oxygen species.

17. The kit of any previous claim, wherein the porous pouch is attachable to the cell encapsulation device.

18. An implantable device comprising:
a porous pouch comprising a bio-absorbable material; and
a cell encapsulation device inside the porous pouch;
wherein the cell encapsulation device is configured to fit inside the porous pouch.

19. The implantable device of claim 8, further comprising a plurality of cells.

20. The implantable device of claim 18 or 19, wherein said cells are microencapsulated.

21. The implantable device of any one claims 18, 19, and 20, wherein the bio-absorbable material is configured to degrade upon contact with moisture.

22. The implantable device of any previous claim, wherein the porous pouch comprises a plurality of pores of a size sufficient to permit growth of vascular tissue from a patient within the plurality of pores.

23. The implantable device of any previous claim, wherein the porous pouch further comprises a water soluble vascularization promoter.

24. The implantable device of any previous claim, wherein the porous pouch and/or the cell encapsulation device are configured to allow insertion and removal of the cell encapsulation device in/from the pouch.

25. The implantable device of any previous claim, wherein the porous pouch is configured to be attached to the cell encapsulation device.

26. The implantable device of any previous claim, wherein said pouch has a sharpened edge or sharpened tips to aid in implantation into a tissue bed.

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods are intended to fall, within the scope of the appended claims. Thus, a combination of steps, elements, components, or constituents can be explicitly mentioned herein; however, all other combinations of steps, elements, components, and constituents are included, even though not explicitly stated.

What is claimed is:

1. A kit for providing a biological therapy to a patient within a tissue bed, the kit comprising:
a cell encapsulation device contained within a first environment, wherein the first environment is a cell-sustaining environment; and
a porous pouch contained in a dry environment,
wherein the cell encapsulation device is configured to fit inside the porous pouch,
wherein the cell-sustaining environment comprises a medium conducive to the subsistence of a plurality of cells, and
wherein the porous pouch is configured to attach to the cell encapsulation device.

2. The kit of claim 1, wherein the medium comprises at least one cell nutrient.

3. The kit of claim 1, further comprising a plurality of cells in said cell-sustaining environment.

4. The kit of claim 3, wherein said cells are microencapsulated.

5. The kit of claim 1, wherein said porous pouch has a sharpened edge or sharpened tips to aid in implantation into a tissue bed.

6. The kit of claim 1, wherein the porous pouch comprises a plurality of pores of a size sufficient to permit growth of vascular tissue from a patient within the plurality of pores.

7. The kit of claim 6, wherein the porous pouch further comprises a non-vascularizing layer comprising a plurality of pores having a pore size that restricts ingrowth of vascular tissues into the plurality of pores.

8. The kit of claim 1, wherein the porous pouch comprises a vascularization promoter.

9. The kit of claim 1, wherein the bio-absorbable material generates reactive oxygen species.

10. A kit comprising:
a cell encapsulation device contained within cell-sustaining environment comprising a medium conducive to the subsistence of a plurality of cells; and
a porous pouch contained within a dry environment containing a desiccant,
wherein the cell encapsulation device is configured to fit inside the porous pouch,
wherein the porous pouch comprises a bio-absorbable material is configured to degrade upon contact with moisture, and
wherein said porous pouch has a sharpened edge or sharpened tips to aid in implantation into a tissue bed.

11. The kit of claim 10, wherein the cell-sustaining environment comprises a medium conducive to the subsistence of a plurality of cells.

12. The kit of claim 10, wherein the medium is an aqueous medium.

13. The kit of claim 10, wherein the bio-absorbable material is configured to degrade upon contact with moisture.

* * * * *